(12) United States Patent
Mark et al.

(10) Patent No.: US 7,137,322 B2
(45) Date of Patent: Nov. 21, 2006

(54) SCREW HOLDER

(75) Inventors: Romano Mark, Davos Dorf (CH); Philipp Büscher, Davos Dorf (CH)

(73) Assignee: Synthes (USA), West Chester, PA (US)

( * ) Notice: Subject to any disclaimer, the term of this patent is extended or adjusted under 35 U.S.C. 154(b) by 0 days.

(21) Appl. No.: 09/824,838

(22) Filed: Apr. 4, 2001

(65) Prior Publication Data

US 2001/0022120 A1    Sep. 20, 2001

Related U.S. Application Data

(63) Continuation of application No. PCT/CH98/00425, filed on Oct. 5, 1998.

(51) Int. Cl.
B25B 23/08    (2006.01)
B25B 23/10    (2006.01)

(52) U.S. Cl. .......................................... 81/452; 81/436

(58) Field of Classification Search .................. 81/436, 81/442, 448, 451, 452
See application file for complete search history.

(56) References Cited

U.S. PATENT DOCUMENTS 1,951,652 A * 3/1934 Fedotoff ..................... 81/448
2,013,826 A * 9/1935 Jacobson ..................... 81/448
3,286,749 A * 11/1966 Learned ...................... 81/448
3,687,179 A * 8/1972 Totsu ......................... 81/448
4,007,768 A * 2/1977 Matsushima ................. 81/448
4,060,114 A   11/1977 Matsushima ................. 145/50
5,237,893 A   8/1993 Ryder et al. ................ 81/452
2001/0022120 A1* 9/2001 Mark et al. .................. 81/452

FOREIGN PATENT DOCUMENTS

DE    19 59 601       6/1970
DE    93 10 668.8     12/1993
EP    0 458 449 A1    11/1991

* cited by examiner

Primary Examiner—Lee D. Wilson
(74) Attorney, Agent, or Firm—Jones Day

(57) ABSTRACT

A screw holder for securing a screw having a longitudinal shank and a central axis, a spindle adjoining the front end of the shank and having a bore therethrough flush with a groove, configured and dimensioned for receiving an elastic component to secure a screw into a steady position while turning the screw in or out.

8 Claims, 3 Drawing Sheets

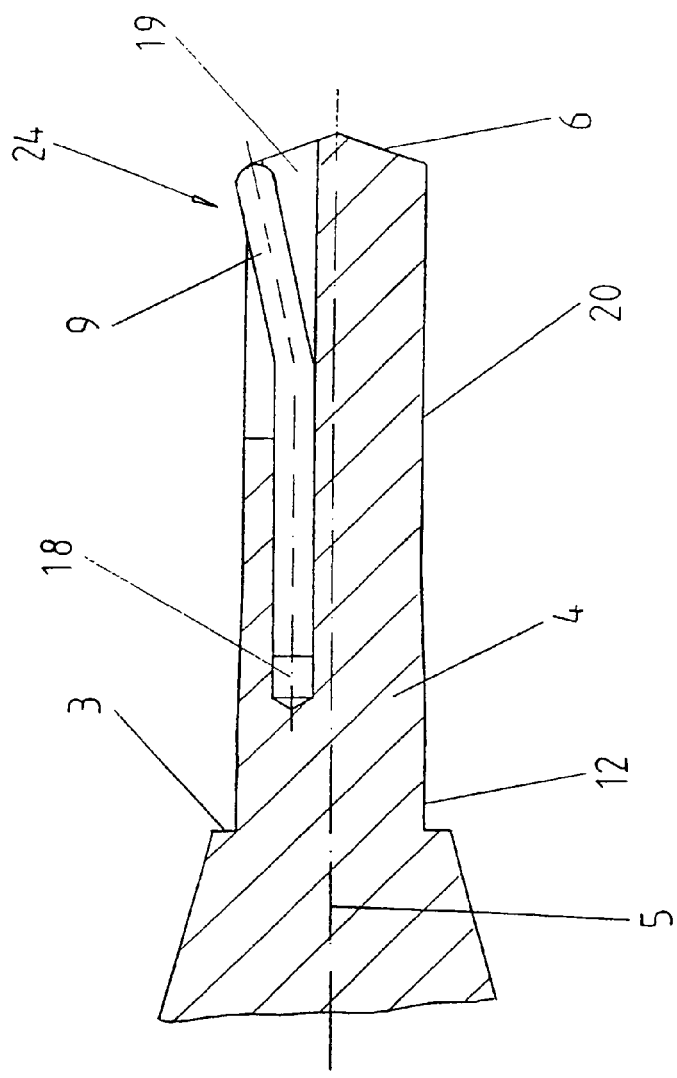
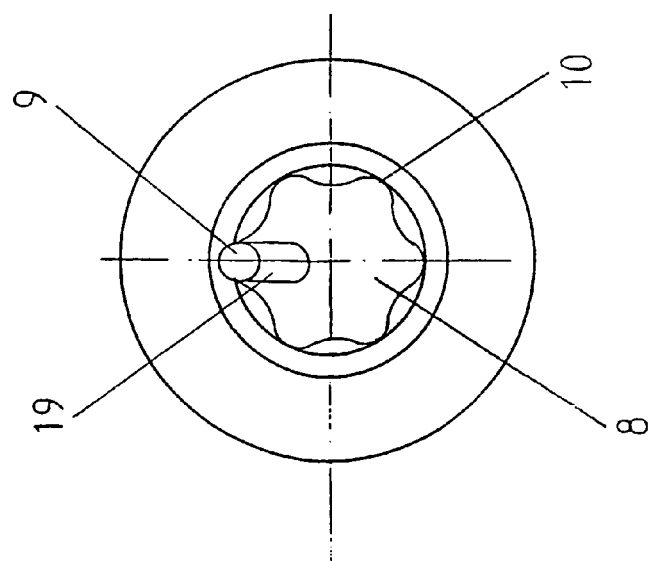
Fig. 4
Fig. 5

SCREW HOLDER

CROSS-REFERENCE TO RELATED APPLICATION

This application is a continuation of International Application No. PCT/CH98/00425, filed Oct. 5, 1998, the disclosure of which is hereby incorporated herein by express reference thereto.

FIELD OF THE INVENTION

This invention is directed to screw holder having a longitudinal shank and a central axis, a spindle located at the front end of the shank, concentric to the central axis, with a bore therethrough and a groove for receiving an elastic component, preferably, a spring, to secure a screw, particularly a bone or pedicle screw. The screw holder can be used during minimally invasive surgery.

BACKGROUND OF THE INVENTION

To lessen the damage to soft parts around bone while surgically implanting a screw inside the body, typically to a bone, joint, or vertebra, the procedure should be carried out without uncovering large areas of the parts to be treated, i.e., smaller incisions and less invasive surgery techniques. The use of clamping tongs to insert bone or pedicle screws is no longer suitable when employing minimally invasive surgery techniques.

European Patent No. 458,449 of Ryder discloses a fastener drive tool for applying a rotational torque to a threaded fastener for driving the fastener into or out of a workpiece. The drive tool has an elongated shaft portion with a free end that is engageable with a recess formed in the fastener. The drive tool has at least one interlobular fastener retention piece attached between two convex partially-cylindrical surfaces that engage a corresponding convex partially-cylindrical surface formed in the fastener recess. The interlobular fastener retention piece retains the fastener on the drive tool when the drive tool is engaged with the fastener recess and prevents wobbling of the fastener when driven by the drive tool, but requires a significant portion of the surface and, therefore, can weaken the cross-section of the shaft, particularly when using smaller screws.

A need exists for a type of screw holder adapted for surgical use. Palliation is a key feature in the design of any surgical tool. A screw holder that might ease the pain typically associated with implantation of a screw into the body, without losing the positive benefits of the surgery, would be beneficial in the art. The present invention aims at solving this need in the art by configuring a screw holder to hold a bone or pedicle screw while being turned in or out.

SUMMARY OF THE INVENTION

The present invention is directed to a device for securing a screw including: a longitudinal shank having a central axis and rear and front ends; a spindle, located at the front end of the longitudinal shank concentric to the central axis, having front and rear ends, a substantially polygonal-shaped cross-section with a plurality of rounded edges and a plurality of concave side surfaces, a groove substantially parallel to the central axis, and a borehole flush with the groove concentric to the central axis; and an elastic component having top and bottom ends, with the bottom end inserted into the borehole and the top end inserted into the groove. Preferably, the shank has a first diameter and the spindle has a second diameter less than the first diameter. The spindle preferably has a hexagonal shape. The elastic component projects transversely to the central axis across the cross-section when unstressed. The spindle is received into a screwhead aperture of the screw, and the screw is secured into position upon stress to the elastic component.

In one embodiment, the rear end of the longitudinal shank is configured and dimensioned to be received into a motor-driven screwdriver. In another embodiment, the rear end of the longitudinal shank is configured and dimensioned to be received by a screwdriver.

In one embodiment, the groove and the borehole are flush with one of the plurality of rounded edges. In another embodiment, the groove and the borehole are flush with one of the plurality of concave side surfaces.

The elastic component can preferably bend elastically substantially perpendicular to the central axis. In one embodiment, the top end of the elastic component is fixed in the groove. In a preferred embodiment, the top end of the elastic component is bonded, soldered, or clamped into the groove. In yet another embodiment, the elastic component is a spring wire, preferably having a width of 2 mm.

The invention is also directed to a method of securing a screw while implanting into a body including: providing a screw having an aperture in a screwhead; providing the device described above; and inserting the spindle into the aperture resulting in stress to the elastic component, wherein upon application of the stress, the elastic component holds the screw in a steady position.

In one embodiment, the screw is a bone or pedicle screw. In another embodiment, the groove and the borehole are flush with one of the plurality of rounded edges. In yet another embodiment, the groove and the borehole are flush with one of the plurality of concave side surfaces.

The elastic component can preferably bend elastically substantially perpendicular to the central axis. In one embodiment, the top end of the elastic component is fixed in the groove, preferably bonded, soldered, or clamped into the groove. The elastic component is preferably a spring wire.

BRIEF DESCRIPTION OF THE DRAWINGS

Further features and advantages of the invention can be ascertained from the following detailed description which is provided in connection with the attached drawings, wherein:

FIG. 4 is a front view according to another embodiment of the invention; and

FIG. 5 is a partial section according to the embodiment of the invention shown in FIG. 4.

DETAILED DESCRIPTION OF THE INVENTION

The present invention relates to a screw holder for securing a bone or pedicle screw, whether being turned in or out, during surgery. The main advantage of the screw holder is that it eliminates the need for the traditionally used clamping tongs and focuses on minimally invasive surgery techniques to reduce the damage to the soft parts around bone while implanting such a screw.

Figure 1:
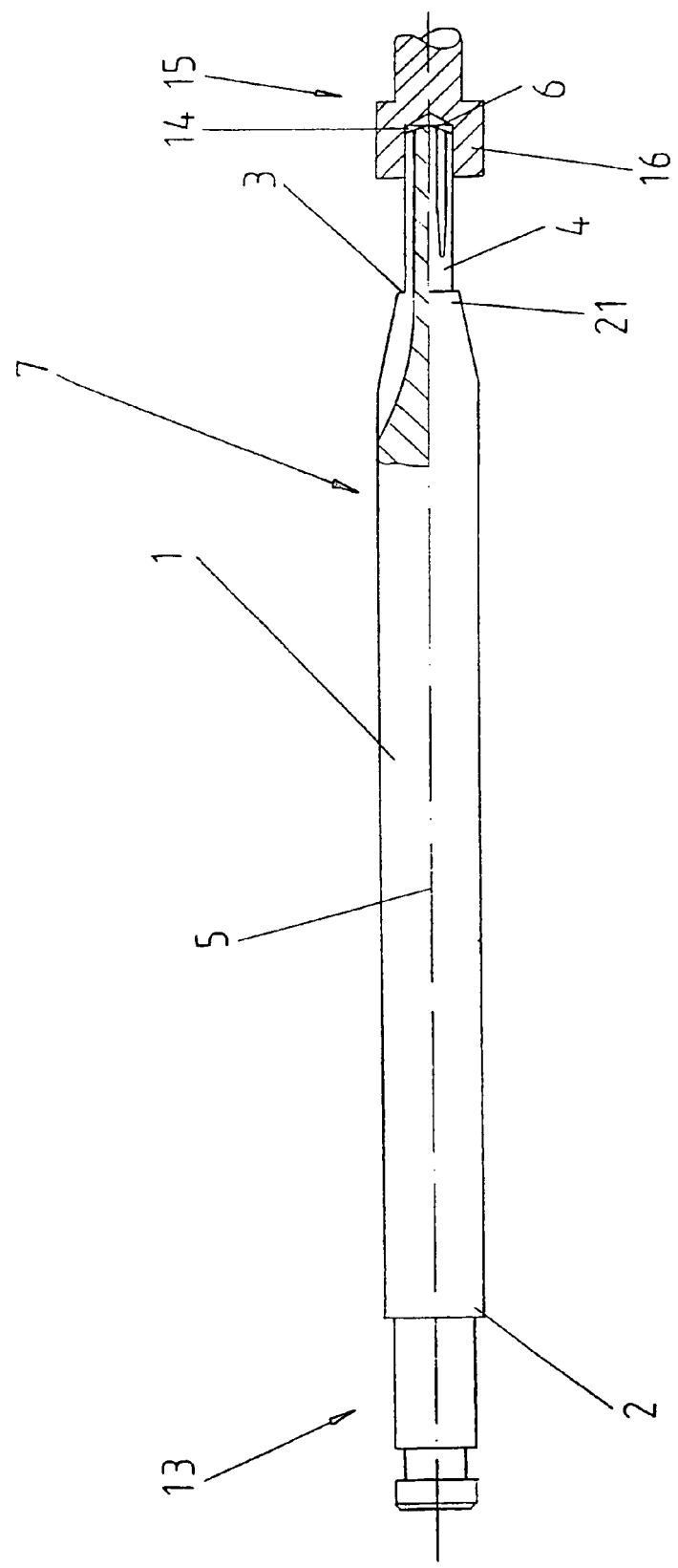
FIG. 1 is a sideview according to one embodiment of the invention.

In one embodiment, shown in FIG. 1, a screw holder 7 includes a cylindrical shank 1 having a central axis 5, a rear end 2 and a front end 21. An affixation means 13 is configured concentrically with the central axis 5 at the rear end 2 of the screw holder 7, allowing the screw holder 7 to be used in a motor-driven screwdriver (not shown). The screw holder can also be handled manually. A spindle 4, concentric with the central axis 5, is present at the front end 21 of the screw holder 7. The diameter of the spindle 4 is less than the diameter of the cylindrical shank 1 resulting in a shoulder 3 formed at the front end 21 of the cylindrical shank 1.

Figure 2:
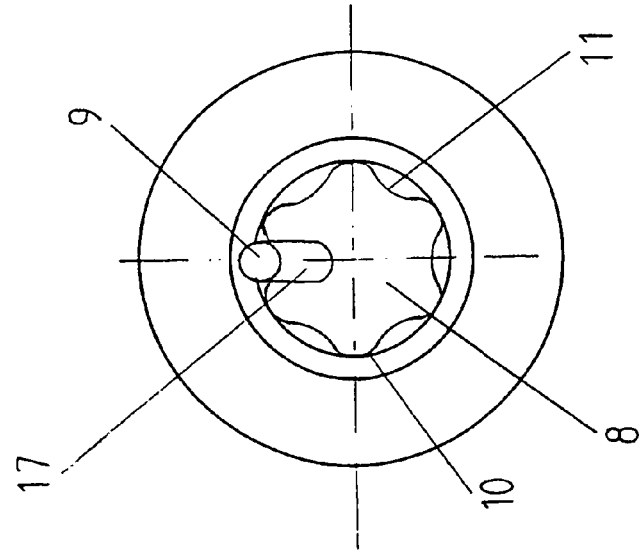
FIG. 2 is a front view according to one embodiment of the invention.

The spindle 4 has a cross-section 8, shown in FIG. 2, configured so that the spindle 4 is insertable into the aperture 14 of a screwhead 16. As a result, a screw 15 is clamped by the spring 9, shown in FIG. 3, against the spindle 4. The spindle 4 is removed from the aperture 14 upon completion of the procedure.

Figure 3:
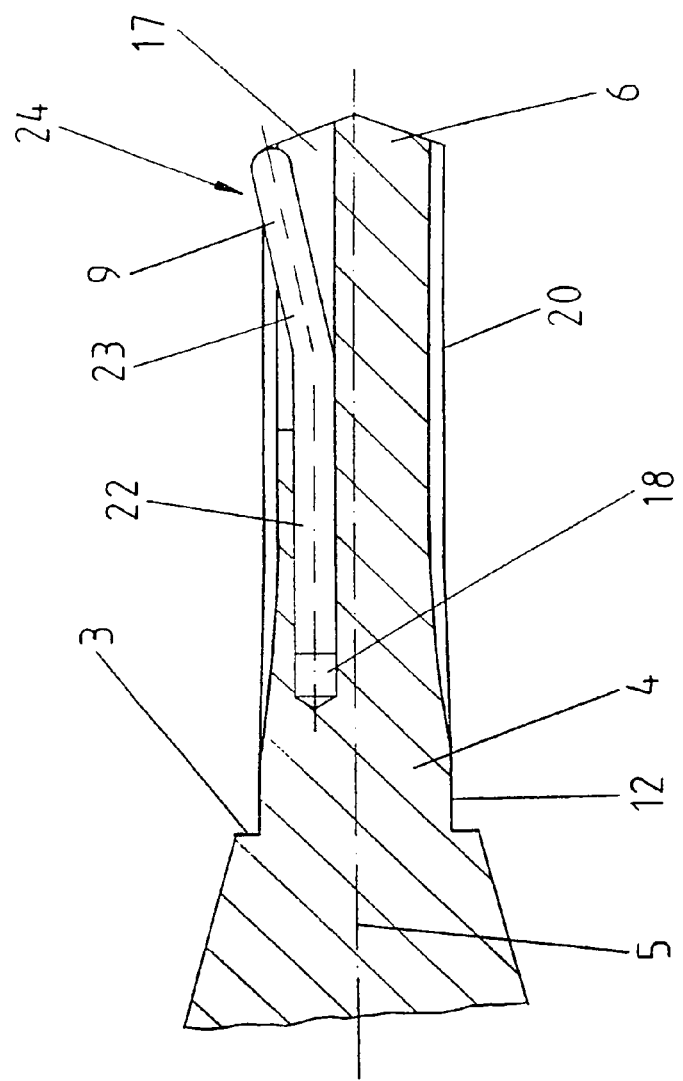
FIG. 3 is a partial section according to the embodiment of the invention shown in FIG. 2.

FIGS. 2 and 3 show an enlargement view of the spindle 4. The spindle includes a front end 6 and a rear end 12, with the rear end 12 adjoining the shoulder 3 formed at the front end 21 of the cylindrical shank 1.

The screw holder spindle can have various cross-sectional shapes, e.g., a hexagonal socket. The spindle 4 preferably has a relatively polygonal-shaped cross-section 8. The polygon corners 10 are rounded and the sides are concave, resulting in rounded edges 20 parallel to the central axis 5. The side surfaces 11 of the spindle 4 are concave and run parallel to the central axis 5. A groove 17 runs parallel to the central axis 5 along one of the concave side surfaces 11. A borehole 18 also runs parallel to the central axis 5 flush with the groove 17 and is configured and dimensioned for receiving a spring 9, thus allowing for a reversible means to secure or clamp the screw while being turned in or out.

The spring 9 may be a leaf spring or another suitable elastic element capable of being adapted for the small diameter of the spindle. In a preferred embodiment, the spring may be a simple spring wire less than 2 mm, and optionally, the spring may be bent. The spring 9 has a clamped part 22 to be located inside the borehole 18; the top part 23, optionally bent, of the spring 9 runs in the groove 17 and projects across the side surface 11 of the spindle 4 transversely to the central axis 5.

The part of the spring 9 providing a means for screw retention 23, in one embodiment being the bent, may be bonded, soldered, or clamped into the groove 17 or 19.

The second embodiment of the invention, shown in FIGS. 4 and 5, relates to the screw holder as described above, with different placement of the groove and borehole for receiving the spring. Groove 19 and borehole 18 are flush along edge 20 of the spindle 4.

It is to be understood that the invention is not to be limited to the exact configuration as illustrated and described herein. For example, the screw holder of the invention may be implemented in various designs using a spring inserted into a groove. The two embodiments discussed in the Detailed Description of the Invention, wherein the groove may be present in an edge of the cross-sectionally polygonal spindle or it may be present in a lateral spindle surface running parallel to the longitudinal axis, are not intended to limit the invention. Accordingly, all expedient modifications readily attainable by one of ordinary skill in the art from the disclosure set forth herein, or by routine experimentation therefrom, are deemed to be within the spirit and scope of the invention as defined by the appended claims.

What is claimed is:

1. A device for securing a screw comprising:
   a longitudinal shank having a central axis and rear and front ends;
   a spindle, located at the front end of the longitudinal shank and concentric to the central axis, having front and rear ends, a substantially polygonal-shaped cross-section with a plurality of rounded edges and a plurality of concave side surfaces, a groove substantially parallel to the central axis, and a borehole coextensive with the groove; and
   a spring wire having top and bottom portions, and a bend positioned between the top and bottom portions, wherein the bottom portion is inserted into the borehole and the top portion is inserted into the groove and has a free end,
   wherein the top portion projects transversely away from the central axis such that the free end of the top portion distal to the bend is further away from the central axis than any other portion of the top portion when the spring wire is unstressed, the spindle being received into a screwhead aperture of the screw so that the top portion of the spring wire secures the screw in position, and wherein the groove and the borehole are flush with one of the plurality of rounded edges and one of the plurality of concave side surfaces.

2. The device of claim 1, wherein the rear end of the longitudinal shank is configured and dimensioned to be received into a motor-driven screwdriver.

3. The device of claim 1, wherein the rear end of the longitudinal shank is configured and dimensioned to be received by a screwdriver.

4. The device of claim 1, wherein the shank has a first diameter and the spindle has a second diameter less than the first diameter.

5. The device of claim 1, wherein the spindle has a hexagonal shape.

6. The device of claim 1, wherein the groove and the borehole are flush with one of the plurality of concave side surfaces.

7. The device of claim 1, wherein the spring wire is bendable substantially perpendicular to the central axis.

8. The device of claim 1, wherein the spring wire has a width of 2 mm.

* * * * *

UNITED STATES PATENT AND TRADEMARK OFFICE
CERTIFICATE OF CORRECTION

PATENT NO. : 7,137,322 B2 Page 1 of 1
APPLICATION NO. : 09/824838
DATED : November 21, 2006
INVENTOR(S) : Mark et al.

It is certified that error appears in the above-identified patent and that said Letters Patent is hereby corrected as shown below:

On the title page,

[*] Notice: Subject to any disclaimer, the term of this patent is extended or adjusted under 35 USC 154(b) by (0) days Delete the phrase "by 0 days" and insert -- by 37 days --

Signed and Sealed this

Twentieth Day of January, 2009

JON W. DUDAS
*Director of the United States Patent and Trademark Office*